US00PP09653P

United States Patent [19]

Wilhelm et al.

[11] Patent Number: Plant 9,653

[45] Date of Patent: Oct. 8, 1996

[54] RASPBERRY PLANT CV. 'WILHELM'

[75] Inventors: Stephen Wilhelm, Alamo; Carlos D. Fear, Aptos, both of Calif.

[73] Assignee: Sweetbriar Development, Inc., Watsonville, Calif.

[21] Appl. No.: 428,644

[22] Filed: Apr. 25, 1995

[51] Int. Cl.[6] ..... A01H 5/00

[52] U.S. Cl. ..... Plt./46.2

[58] Field of Search ..... Plt./46.2

*Primary Examiner*—James R. Feyrer

*Attorney, Agent, or Firm*—Synnestvedt & Lechner

[57] ABSTRACT

A new and distinct cultivar of red raspberry plant named 'Wilhelm', which is particularly characterized and distinguished by its very attractive fruit and its high yielding capacity on both primocane and floricane crops.

3 Drawing Sheets

BACKGROUND AND SUMMARY OF THE NEW CULTIVAR

This invention relates to a new and distinct cultivar of raspberry plant that has been given the cultivar name or denomination 'Wilhelm'. The new cultivar was developed from hybridization of the selection B175–3 (an unpatented proprietary cultivar) as the seed parent with the selection B8–4 (an unpatented proprietary cultivar) as the pollen parent. The parents were crossed by Stephen Wilhelm in 1986, whereafter fruit and seed were collected to produce seedlings for field planting in Watsonville, Calif. in 1988. The new cultivar was selected from these seedlings by Carlos Fear in 1989 for its ease of harvest and attractive, well-flavored fruit. Since its selection the 'Wilhelm' plants have been evaluated in noncommercial experimental plantings in Oxnard and Watsonville, Calif. The cultivar has been asexually propagated by in vitro shoot tip culture, root sucker division and root cuttings, and has been shown to maintain the desired and distinguishing characteristics after propagation over several generations.

The 'Wilhelm' raspberry plant produces a mid-season primocane crop which begins in mid August and continues until early-mid November. The floricane crop begins in mid-late May and continues until early July. Both the primocane and floricane yields (about 7.4 to 11.8 T/acre and about 4.7 to 8.8 T/acre, respectively) are high relative to other comparable cultivars. The fruit of the 'Wilhelm' raspberry plant is very attractive, with small drupelets of a bright red color which darkens only slightly after harvest.

DETAILED DESCRIPTION OF THE NEW CULTIVAR

Figure 1:
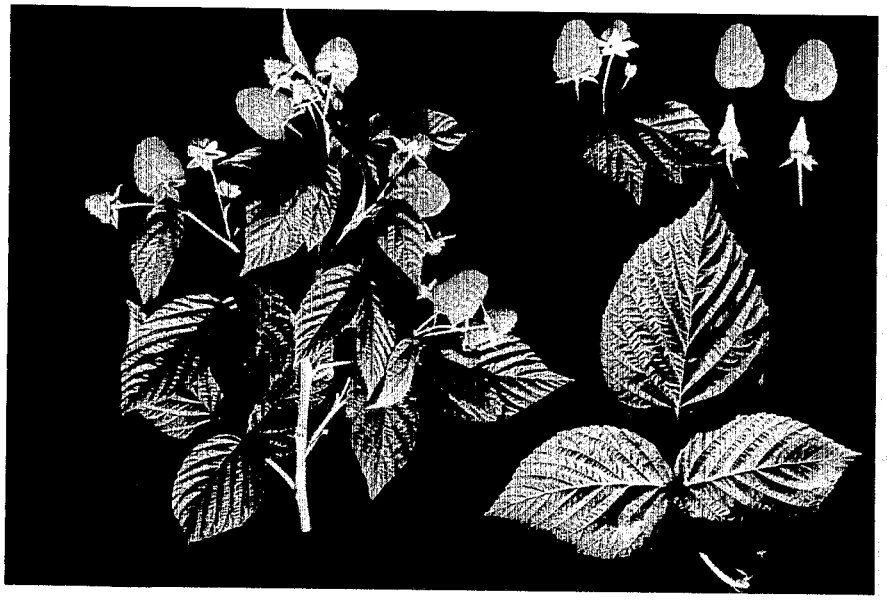
FIG. 1 is a photograph of a 'Wilhelm' primocane mature leaf and fruiting shoot, showing various stages of fruit development.
Figure 2:
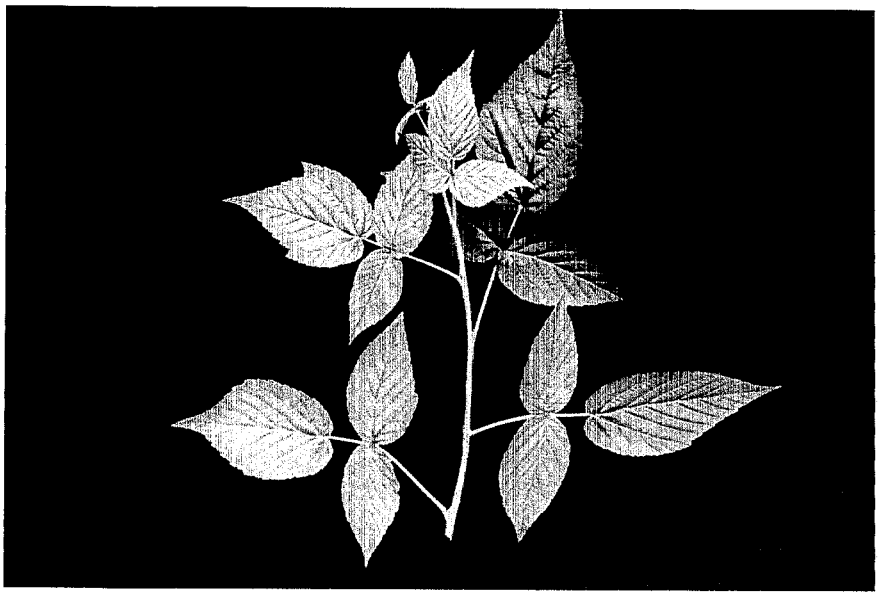
FIG. 2 is a photograph of a 'Wilhelm' primocane shoot.

Throughout this specification, color names beginning with a small letter signify that the name of the color, as used in common speech, is aptly descriptive. Color names beginning with a capital letter designate color values based on the R.H.S. Colour Chart published by The Royal Horticultural Society of London, England.

The following description is a detailed description of the 'Wilhelm' raspberry cultivar and the fruit produced thereby, as grown in Watsonville, Calif. between 1991 and 1994, and is believed to apply to plants of the 'Wilhelm' cultivar grown in similar conditions of soil and climate elsewhere.

The 'Wilhelm' fruit size on the primocane crop starts out large and declines as the harvest season progresses. The fruit size of the floricane crop is smaller with only a slight decline as the harvest progresses seasonally. The fruit of the 'Wilhelm' plant is light red, releases very easily from its receptacle, and is of moderate firmness at harvest. Post harvest fruit rot resistance is intermediate in comparison with many other selections and cultivars.

The 'Wilhelm' cultivar has moderate susceptibility to late leaf rust and powdery mildew. Resistance to root rots is unknown and cold tolerance of the new cultivar has not been established.

The new cultivar is particularly characterized and distinguished from other cultivars by its very attractive fruit of excellent shape with small drupelets. It is further distinguished by its bright, light red fruit color and ease of harvest. The 'Wilhelm' cultivar also yields more on both primocanes and floricanes than most other known cultivars.

'Wilhelm' is distinguished from its pollen parent, selection B8–4, by having larger fruit size and greater susceptibility to late leaf rust. The new cultivar is distinguished from its seed parent, selection B175–3, by having a higher yielding capacity with more uniform fruit shape, having greater resistance to late leaf rust and having less tendency to darken after harvest.

Tables 1 and 2 below present relevant morphological information about the new raspberry 'Wilhelm' cultivar.

TABLE 1

PLANT CHARACTERISTICS OF 'Wilhelm'

| | |
|---|---|
| General | |
| Plant size: | medium |
| Growth habit: | erect |
| Density of foliage: | medium |
| Productivity: | above average |
| Self fruitfulness: | self fruitful |
| Primocane fruiting: | |
| percent of cane length flowering as primocane: | about 20–25% |
| percent of total yield from primocane crop: | about 30–50% |
| Suckering tendency: | low |
| Utility of fruit: | various |

TABLE 1-continued

| PLANT CHARACTERISTICS OF 'Wilhelm' | |
|---|---|
| Canes | |
| Primocanes | |
| Number of fruiting laterals/cane: | about 8–14 |
| Number of canes/crown: | about 3–18 |
| Young shoot pigmentation: | weak–medium |
| Length: | about 67–72" |
| Diameter (end of 1st year): | |
| cane base: | about 0.34–0.53" |
| central ⅓ of cane: | about 0.31–0.47" |
| Depressions in cross section: | absent |
| Prickles: | |
| pigmentation: | unpigmented |
| density on young shoots: | very few |
| attitude of tip: | horizontal |
| size: | small |
| texture: | soft |
| presence and distribution on petioles: | irregularly distributed |
| Pubescence on canes: | present |
| Internodal distance (at central ⅓ of cane): | about 1.4–2.2" |
| Lenticels: | not visually detectable |
| Floricanes | |
| Length: | about 42–70" |
| Number nodes/lateral (at mid cane): | about 8–12 |
| Number of flowers/node (at 4th node from apex on a mid cane lateral): | about 1–3 |
| Leaves | |
| Arrangement: | compound |
| Relief between veins: | medium |
| Leaflet number: | 3–5, usually 3 |
| Terminal leaflet: | |
| length: | about 4.6–5.4" |
| width: | about 2.9–3.8" |
| shape: | ovate |
| tip: | acute to acuminate |
| base: | rounded to cordate |
| margin: | doubly serrate |
| Lateral leaflets (basal pair): | |
| overlap: | touching to slight overlap |
| orientation: | opposite |
| shape: | ovate |
| tip: | acute to acuminate |
| base: | rounded |
| margin: | doubly serrate |
| length: | about 3.5–4.9" |
| width: | about 2.0–2.8" |
| Rachis length between terminal leaflet and adjacent lateral leaflets: | about 1.2–1.4" |
| Color: | |
| face: | Green 137B |
| underslide: | Greyed-Green 191C |
| Petiole: | |
| length: | about 2.5–5.3" |
| pigmentation of upper surface: | pigmented |
| pigmentation of underside: | unpigmented |
| Stipule orientation: | erect |
| Flowers | |
| Flowering period: | |
| primocane: | early June to October |
| floricane: | late March to early June |
| Petal: | |
| color: | White 155D |
| length: | about 0.22–0.28" |
| width: | about 0.09–0.13" |
| number: | 5 |
| arrangement: | free |
| Pedicel coloration: | absent to very weak |

TABLE 2

| FRUIT CHARACTERISTICS OF 'Wilhelm' | |
|---|---|
| Fruit | |
| Harvest season: | |
| primocane: | mid-season; begins mid August; ends early to mid November; ripens uniformly over a long period (about 75–110 days) |
| floricane: | early to mid-season; normally begins mid to late May; ends early July; ripens uniformly over about a 45–55 day period |
| Color: | |
| immature: | Red 39A |
| maturing: | Red 47A |
| mature: | Red 53A–53B |
| Dimensions: | |
| weight: | |
| primocane harvest: | about 2.2–5.0 g (3.1 g mean) |
| floricane harvest: | about 2.3–3.5 g (2.7 g mean) |
| length (primocane): | about 0.71–0.91" |
| width (primocane): | about 0.62–0.72" |
| Soluble solids (%): | about 8.1–10.6% (9.5% mean) |
| Titratable acidity (% as citric acid): | about 1.9% |
| Seeds: | |
| weight: | about 1.0–1.6 mg (1.3 mg mean) |
| Number drupelets/fruit: | about 83–146 (109 mean) |

Figure 3:
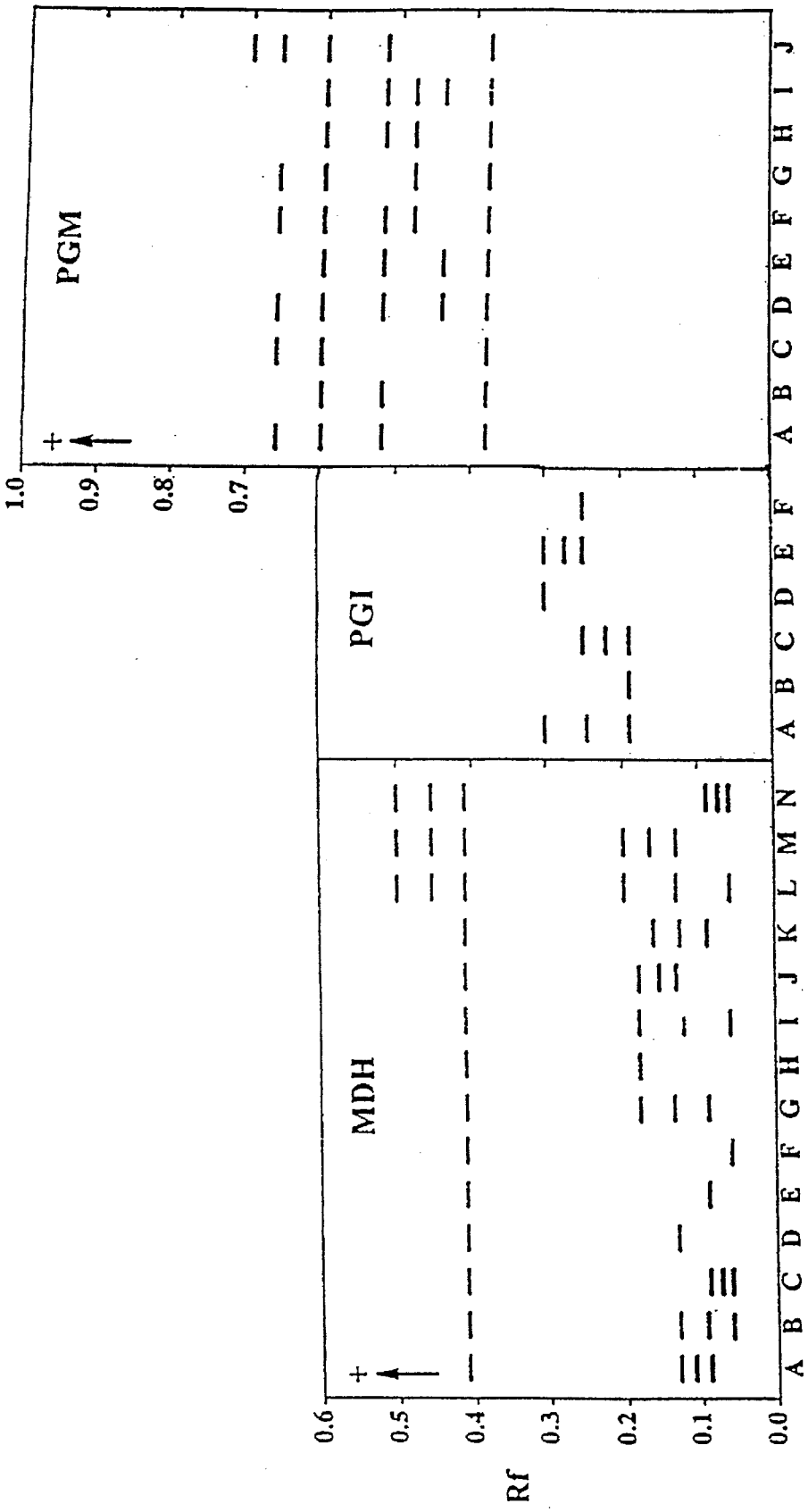
FIG. 3 is an interpretative drawing showing the cultivar banding patterns for the enzymes, MDH (malate dehydrogenase), PGI (phosphoglucoisomerase) and PGM (phosphoglucomutase).

In addition to the foregoing morphological description, and to provide further means for identifying the new cultivar and distinguishing it from some other somewhat similar and/or related raspberry cultivars, the new 'Wilhelm' cultivar has been analyzed to obtain an indication of its genetic makeup. Specifically, leaves of the 'Wilhelm', 'Hollins' (U.S. Plant Pat. No. 8,027), 'Summit' (unpatented), 'Isabel' (U.S. Plant patent applied for), 'Sweetbriar' (U.S. Plant Pat. No. 4,486), 'Joe Mello' (U.S. Plant Pat. No. 6,493) and 'Godiva' (U.S. plant patent applied for) cultivars were electrophoretically analyzed, the patterns designated and procedures utilized being per those described by J. C. Cousineau and D. J. Donnelly, "Use of Isoenzyme Analysis to Characterize Raspberry Cultivars and Detect Cultivar Mislabeling," *HortScience,* vol. 27 (9):1023–1025 (1992). The results of the electrophoresis analysis are presented in Table 3 below, the letters representing the cultivar banding patterns for each enzyme as shown in FIG. 3, taken from the above article.

TABLE 3

ISOZYME BANDING PATTERNS OF 'Wilhelm' COMPARED WITH 'Hollins', 'Summit', 'Isabel', 'Sweetbriar', 'Joe Mello' AND 'Godiva'

| | Isozyme | | |
|---|---|---|---|
| Cultivar | PGI | MDH | PGM |
| 'Wilhelm' | D | A | C |
| 'Hollins' | D | E | D |
| 'Summit' | A | C | B |
| 'Isabel' | A | E | C |
| 'Sweetbriar' | D | D | A |
| 'Joe Mello' | D | E | C |
| 'Godiva' | B | A | D |

We claim:

1. A new and distinct cultivar of raspberry plant named 'Wilhelm', as herein illustrated and described.

* * * * *